United States Patent
Winkelmann

Patent Number: 5,512,761
Date of Patent: Apr. 30, 1996

[54] DISTANCE SENSOR FOR DETERMINING A DISTANCE BETWEEN TWO RELATIVELY MOVABLE MEMBERS BY MEASURING A TIME DURING WHICH A MEASURING MARK IS IN A LIGHT PATH BETWEEN A LIGHT TRANSMITTER AND A LIGHT RECEIVER

[75] Inventor: Helmut Winkelmann, Forchheim, Germany

[73] Assignee: Siemens Aktiengesellschaft, Munich, Germany

[21] Appl. No.: 296,590

[22] Filed: Aug. 29, 1994

[30] Foreign Application Priority Data

Sep. 22, 1993 [DE] Germany ............... 43 32 254.9

[51] Int. Cl.$^6$ .................................................. G01N 21/00
[52] U.S. Cl. ....................... 250/559.38; 250/559.44; 250/559.27; 356/375
[58] Field of Search ............... 250/559.38, 557.40, 250/559.44, 559.27, 231.13, 231.17; 356/375

[56] References Cited

U.S. PATENT DOCUMENTS

| | | | |
|---|---|---|---|
| 3,922,539 | 11/1975 | Carnes et al. | 250/559.44 |
| 4,703,424 | 10/1987 | Gullberg et al. | |
| 4,788,441 | 11/1988 | Laskowski | 250/559.38 |
| 4,812,983 | 3/1989 | Gullberg et al. | |
| 4,864,631 | 9/1989 | Jensen | 250/559.44 |
| 4,926,049 | 5/1990 | Nakamura et al. | 250/559.44 |
| 4,928,008 | 5/1990 | Huggins et al. | 356/375 |

FOREIGN PATENT DOCUMENTS

| | | |
|---|---|---|
| 256910 | 5/1988 | German Dem. Rep. . |
| 1197236 | 10/1969 | Germany . |
| 1215384 | 12/1969 | Germany . |

*Primary Examiner*—Edward P. Westin
*Assistant Examiner*—Steven L. Nichols
*Attorney, Agent, or Firm*—Hill, Steadman & Simpson

[57] ABSTRACT

A distance sensor is provided for supplying a precise distance signal identifying the spacing between two components in a computed tomography apparatus which move relative to each other. The two components may be, for example, the rotating scan frame and the stationary gantry inside of which the scan frame rotates. The distance sensor includes a measuring mark mounted on one of the components and having a geometrical shape, such as the shape of a triangle tapering toward the other component, so that the measuring mark influences, such as by interrupting, the path of a measuring light ray which is emitted from the other of the components. The time during which the measuring mark influences the measuring light ray is dependent on the spacing of the components from each other. A signal indicative of this spacing is supplied to an evaluation circuit, and can be used to identify deviations from a specified rotational center of the scan frame with a high degree of resolution, so that appropriate correction steps can be undertaken.

5 Claims, 2 Drawing Sheets

DISTANCE SENSOR FOR DETERMINING A DISTANCE BETWEEN TWO RELATIVELY MOVABLE MEMBERS BY MEASURING A TIME DURING WHICH A MEASURING MARK IS IN A LIGHT PATH BETWEEN A LIGHT TRANSMITTER AND A LIGHT RECEIVER

BACKGROUND OF THE INVENTION

1. Field of the Invention

The present invention is directed to a distance sensor for providing an electrical signal identifying a spacing between two components, and in particular to a distance sensor suitable for use in a computed tomography apparatus for measuring the distance between two components which are moved relative to one another.

2. Description of the Prior Art

A problem exists in the design and operation of computed tomography systems to maintain a precise positioning of the rotational center of the rotating scan frame, the scan frame rotating inside a stationary (non-rotating) gantry. The scan frame rotates inside the gantry with a clearance or spacing between the gantry and the scan frame, and one way to monitor the position of the rotational center is to identify any changes in the spacing between the rotating scan frame and the stationary gantry.

German Patentschrift 12 15 384 discloses an arrangement for non-contacting measurement of the axial displacement of a shaft relative to a fixed point. In this known arrangement, a measuring mark, which influences the path of a measuring radiation (light) ray, is attached to the shaft. The measuring mark has a geometrical shape which is designed so that the duration of a signal which is generated while the mark is influencing the path of the measuring ray is dependent on the amount of displacement of the shaft. This arrangement, however, is not suitable for determining migration of the rotational center of a computed tomography apparatus from a specified position, because such migration takes place in a radial direction.

SUMMARY OF THE INVENTION

It is an object of the present invention to provide a distance sensor which has a simple structure and which permits a distance between two components which are movable relative to each other to be identified with a high degree of precision.

It is a further object of the present invention to provide such a distance sensor which permits migration of the position of the rotational center of the rotating scan frame in a computed tomography apparatus to be identified.

The above object is achieved in accordance with the principles of the present invention in a distance sensor for identifying the position of the rotational center of a rotating component in a computed tomography apparatus which rotates relative to a stationary component, wherein a measuring mark is disposed on one of the components and a light transmitter and a light receiver are disposed on the other of the components, the measuring mark influencing the path of a measuring ray from the transmitter and having a geometrical shape so that a duration of the influencing of the path of the measuring ray is dependent on the distance between the components. The distance signal can be supplied to an evaluation circuit for identifying the position of the rotational center.

Preferably, the measuring mark has a triangular shape, and is disposed so as to tape from a widest portion on the component on which it is mounted to a narrowest portion pointing toward the other component. Preferably, the influencing of the path of the measuring ray is an interruption of the measuring ray by the measuring mark. The duration of the interruption is dependent on the spacing between the two components. Consequently, the spacing can be identified from the measured interruption duration.

In a preferred embodiment of the invention, two measuring marks are disposed side-by-side on one of the components. The distance sensor in this embodiment is thus insensitive to tilting or twisting as well as two variations in the relative velocity of the two components, i.e., fluctuations in the rotational speed.

DESCRIPTION OF THE PREFERRED EMBODIMENTS

Figure 1:
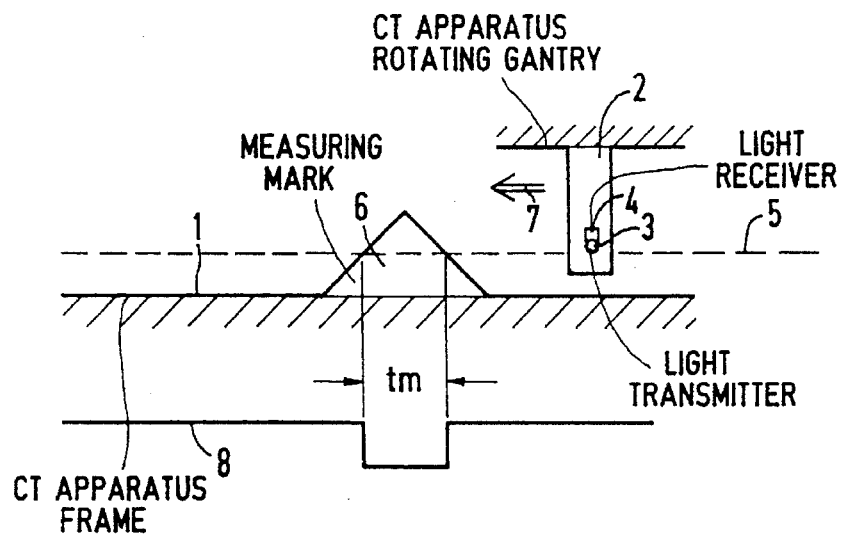
FIG. 1 is a schematic illustration of a distance sensor constructed in accordance with the principles of the present invention.

A portion of a stationary component 1 and a moving component 2 of a computed tomography apparatus are shown in FIG. 1. The apparatus of which the components shown in FIG. 1 are a part has a known structural configuration of a scan frame which rotates in a stationary gantry, the scan frame having a rotational center around which it rotates. The stationary component 1, therefore, is a portion of the gantry and the moving component 2 is a portion of the scan frame.

A light transmitter 3 and a light receiver 4 are, in the embodiment shown in FIG. 1, mounted on the component 2 so that as the component 2 moves, the light receiver and the light transmitter exhibit a movement path as indicated by the dashed line 5. a triangular measuring mark 6 is mounted on the component 1 in the embodiment of FIG. 1, with an apex of the triangle pointing toward the component 2. The measuring mark 6, and the light receiver 4 and light transmitter 3, are disposed in respectively different planes, so that as the light transmitter 3 and the light receiver 4 move along the path described by the dashed line 5, they will pass by (in the embodiment of FIG. 1, behind) the measuring mark 6.

When the component 2 is moved in the direction of the arrow 7, a light ray, which is continuously emitted by light transmitter 3, will be reflected off of a surface of the measuring mark 6 facing the light transmitter 3 onto the light receiver 4 as the light transmitter 3 and the light receiver 4 pass by the measuring mark 6. The light ray will be reflected during a time tm. Since the measuring mark 6 tapers toward the component 2, the duration of the time tm will be dependent on the width of the triangular measuring mark 6 at the level of the light transmitter 3 and the light receiver 4. This width, in turn, is dependent on the spacing between the moving component 2 and the stationary component 1 at the time the light transmitter 3 and the light receiver 4 pass by the measuring mark 6.

The light receiver 4 consequently generates an electrical output signal having a pulse-like waveform, as indicated by the curve 8 in FIG. 1. The signal having the curve 8 can then be analyzed, as described in detail below, to precisely identify the spacing between the stationary component 1 and the moving component 2.

The embodiment shown in FIG. 1 is for exemplary purposes; the relative positioning of a light transmitter 3, the light receiver 4 and the measuring mark 6 can be rearranged, i.e., the measuring mark 6 may be disposed on the moving component 2 and the light transmitter 3 and the light receiver 4 may be mounted on the stationary component. It is also possible to arrange the light transmitter 3 and the light receiver 4 so that they respectively pass by opposite sides of the measuring mark 6, in which case the duration of the interruption of the light ray by the measuring mark 6 will indicate the spacing between the moving component 2 and the stationary component 1, instead of the duration of the reflection of the light ray.

The above-described principle can be applied to linear motions as well as to rotating motions.

Figure 2:
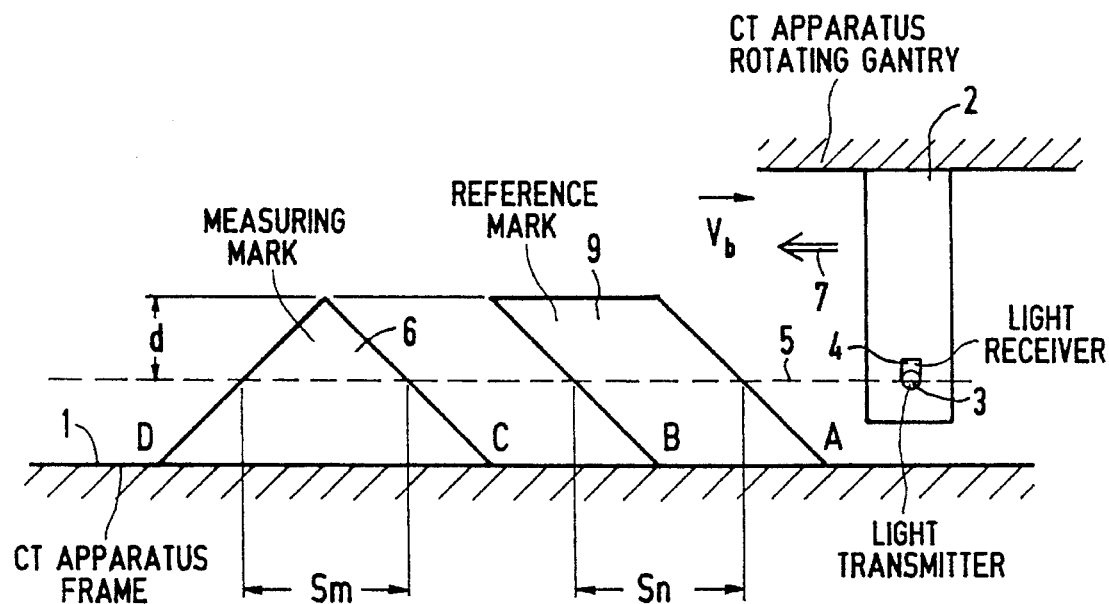
FIG. 2 is a schematic illustration of a further embodiment of the distance sensor constructed in accordance with the principles of the present invention.

As shown in FIG. 2, a second measuring mark 9, which serves as reference measuring mark, can be mounted next to the measuring mark 6. When the quotient of the respective pulse durations produced by the interaction of the light ray with the measuring marks 6 and 9 is formed, the distance sensor is then insensitive to tilting or twisting assembly imprecisions, as well as being insensitive to changes in the absolute velocity of the moving component 2, for example, speed fluctuations, insofar as none of these variations occur during the actual measurement.

In the arrangement of the measuring marks 6 and 9 shown in FIG. 2, the following relationship is valid for identifying the distance d:

$$d = \frac{tm}{tn} \times \frac{sn}{2}$$

with the condition that sides A, B and C are all parallel, and side C is perpendicular to side D, and wherein:

d: Distance (measured quantity)
tm: Interruption time of the measuring mark
tn: Interruption time of the reference mark
Sm: Interruption path of the measuring mark
Sn: Interruption path of the reference mark
Vb: Path velocity.

By evaluating the distance signal generated by the light receiver 4 with respect to its amplitude, a level can be acquired, for example 50% of maximum amplitude, at which it is assumed that a light/dark, or non-interrupted/interrupted, transition has occurred. The distance sensor therefore always evaluates the respective positions of the leading and trailing edges of a pulse in the distance signal at the same geometrical location of the edge of the measuring mark 6 or 9. This is advantageous in the case of light beam which, due to aging of components or transient conditions, may generate a light beam with a slight spread, which would result in blurred transitions.

This conditions can also be used to monitor the light transmitter 3 to determine whether and when the light transmitter 3 has aged to an extent so as to be no longer useable, or if an optical defect (contamination) is present.

By arranging the edges of the mark 9 obliquely, the same optical/electrical transmission behavior as in the case of the mark 6 is achieved.

Since these time measurements can be very precisely implemented, a good spatial resolution results therefrom. As a practical matter, the measuring time amounts to approximately 2.8 ms, the chronological resolution amounts to 1 μs, the path velocity is approximately 3.6 m/s, and the resulting spatial resolution is approximately 5 μm. An increase in the chronological resolution 2, for example, 100 ns enhances the spatial resolution to a value below 0.5 μm.

The above-described distance sensor can be employed in a rotating gantry-type computed tomography apparatus in order to monitor changes in the position of the rotational center of the gantry with a resolution of 1/100 of a millimeter, in order to initiate appropriate correction steps.

Figure 3:
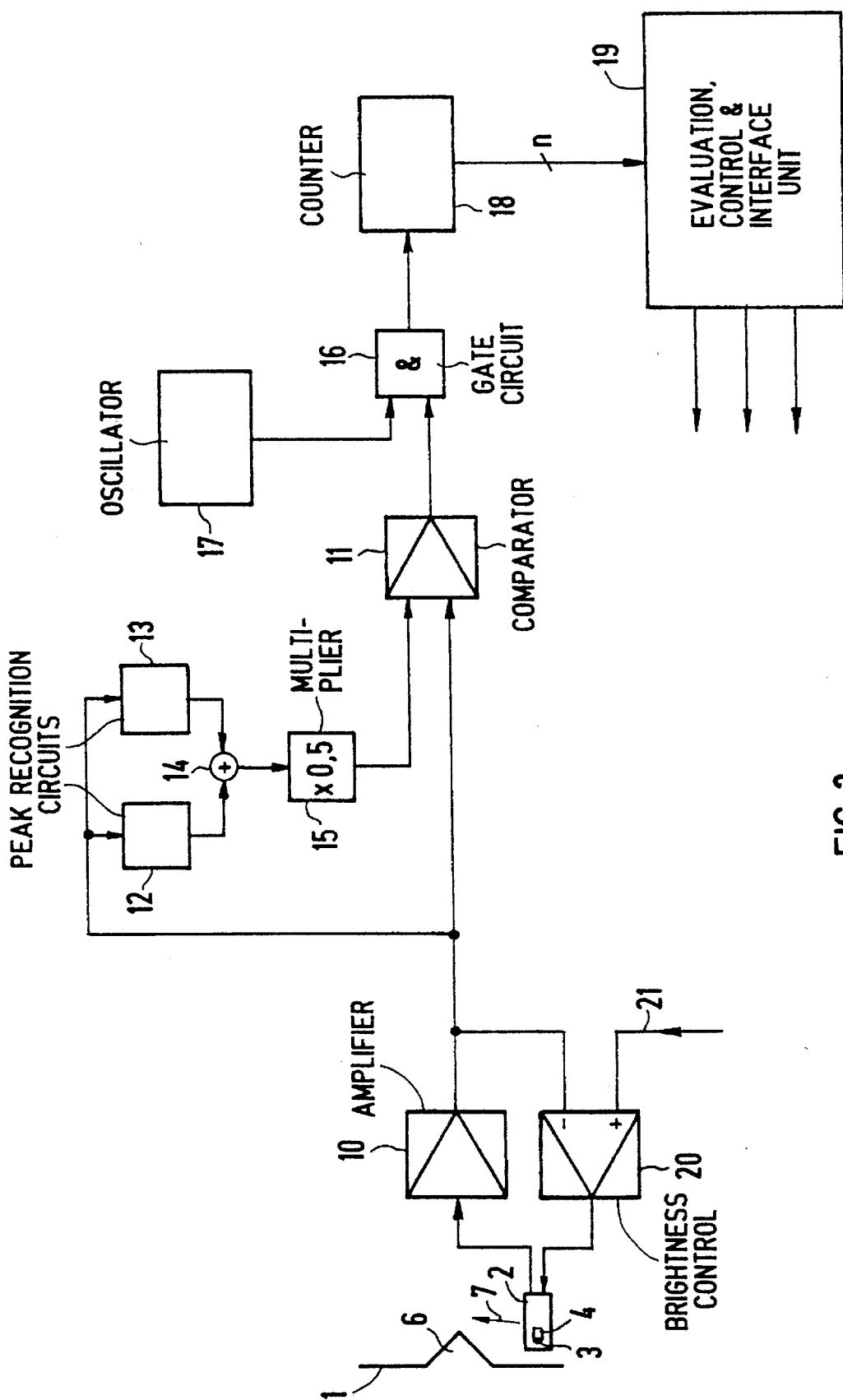
FIG. 3 is a circuit diagram for evaluation electronics for use with the structural portions of the distance sensor shown in FIG. 1.

An evaluation circuit for accomplishing such monitoring is shown in FIG. 3. The output signal from the arrangement shown either in FIG. 1 or FIG. 2 is supplied to an amplifier 10, and the amplified distance signal is then supplied to a comparator 11 as well as to a recognition circuit 12 for identifying the positive peak of the signal and to a recognition circuit 13 for identifying the negative peak of the signal. The output signals of the recognition circuits 12 and 13 are supplied to an adder 14. The output signal of the adder 14 is supplied through a multiplier 15 to the comparator 11 as a reference signal. The output signal of the comparator 11 controls a gate circuit 16, such as an AND gate, whose other input is connected to an oscillator 17, which produces a signal, for example, at 1 MHz. The gate circuit 16 controls a counter 18 whose output signal is supplied to an evaluation, control and interface unit 19. The outputs of the evaluation, control and interface unit 19 can be corrected to appropriate mechanical and electrical components to take whatever corrective steps may be necessary to re-position the components 1 and 2 relative to each other in the event that the distance signal indicates that the gantry has deviated from a position corresponding to rotation around the specified rotational center.

The output of the amplifier 10 is also supplied to one input of a brightness regulator 20, the output of which is supplied to the light transmitter 3. A reference value is supplied to an input 21 of the brightness regulator 20, so that the light transmitter 3 can always be operated so as to produce an output signal at a constant baseline level.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computed tomography apparatus comprising: first and second components which are movable relative to one another and which are spaced a distance from each other;

a light transmitter and a light receiver mounted on one of said components and having a light path therebetween;

a measuring mark mounted on the other of said components, said measuring mark being disposed to temporarily move into said light path as said measuring mark passes said light receiver and light transmitter as said components move relative to each other, and said measuring mark having a shape for changing a duration of incidence of light from said light transmitter on said light receiver, when said measuring mark is in said light path, dependent on the distance between said components;

said light receiver generating a distance signal having a signal parameter which is representative of said duration; and means for evaluating said signal parameter of said distance signal for identifying the distance between said components therefrom.

2. A computed tomography apparatus as claimed in claim 1 wherein said measuring mark has a triangular shape acutely tapering from the component on which it is mounted toward the other of said components.

3. A computed tomography apparatus as claimed in claim 1 further comprising a reference mark mounted spaced from said measuring mark on the same component as said measuring mark and also disposed to temporarily move into said light path as said two components move relative to each other, said light receiver generating a reference signal having a signal parameter which is representative of said reference duration, said reference mark having a shape for producing a reference duration of incidence flight from said light transmitter on said light receiver, when said reference mark is in said light path, which is independent of said distance between said components, and wherein said means for evaluating comprises means for evaluating said signal parameter of said distance signal divided by said signal parameter of said reference signal for identifying the distance between said components.

4. A computed tomography apparatus as claimed in claim 1 wherein said distance signal has an amplitude comprising said signal parameter, and wherein said evaluation means comprises means for determining said duration by identifying when the amplitude of said distance signal exceeds and falls below a predetermined level.

5. A computed tomography apparatus as claimed in claim 1 wherein said first component comprises a stationary gantry and said second component comprises a scan frame rotating in said stationary gantry around a predetermined rotational center, and wherein said evaluation means comprises means for using said distance to identify deviations in a current rotational center of said scan frame from said predetermined rotational center.

* * * * *